United States Patent [19]
Fischer et al.

[11] 4,257,859
[45] Mar. 24, 1981

[54] BENZOIN PHOTOINITIATOR CONTAINING A QUATERNARY AMMONIUM GROUP IN PHOTO CURABLE COMPOSITION AND PROCESS

[75] Inventors: Martin Fischer; Werner Kuesters; Erich Penzel; Wolfgang Rehder; Walter Trautmann, all of Ludwigshafen, Fed. Rep. of Germany

[73] Assignee: BASF Aktiengesellschaft, Fed. Rep. of Germany

[21] Appl. No.: 57,084

[22] Filed: Jul. 12, 1979

[30] Foreign Application Priority Data

Jul. 15, 1978 [DE] Fed. Rep. of Germany ....... 2831263

[51] Int. Cl.$^3$ ............................................... C08J 3/28
[52] U.S. Cl. .......................... 204/159.23; 204/159.24; 260/29.6 MM; 260/326.5 S; 260/326.5 E; 430/914; 430/919; 430/920; 526/208; 544/175; 546/237; 564/285; 564/287
[58] Field of Search .................. 526/208; 204/159.24, 204/159.23; 430/914, 919, 920, 281; 260/567.6 M, 326.5 S, 29.6 MN

[56] References Cited
U.S. PATENT DOCUMENTS

| | | | |
|---|---|---|---|
| 2,666,025 | 1/1954 | Nozaki | 204/158 |
| 3,001,922 | 9/1961 | Zimm | 204/162 |
| 3,631,009 | 12/1971 | Meyer | 526/208 |
| 3,915,823 | 10/1975 | Rudolph et al. | 204/159.23 |
| 3,933,682 | 1/1976 | Bean | 430/919 |
| 4,007,209 | 2/1977 | Hickmann et al. | 204/159.23 |
| 4,082,821 | 4/1978 | Schmidt et al. | 204/159.23 |

*Primary Examiner*—John C. Bleutge
*Assistant Examiner*—A. H. Koeckert
*Attorney, Agent, or Firm*—Keil & Witherspoon

[57] ABSTRACT

Quaternary ammonium compounds of the formula

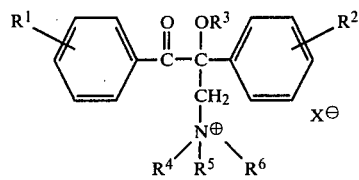

where
$R^1$ and $R^2$ are identical or different and each is H, halogen, phenyl, alkyl, alkoxy or alkylthio,
$R^3$ is H or alkyl, hydroxyalkyl, cycloalkyl or aralkyl,
$R^4$ and $R^5$ are identical or different and each is alkyl, phenyl, cycloalkyl or aralkyl or
$R^4$ and $R^5$ together are a —(CH$_2$)$_4$— bridge, a —(CH$_2$)$_5$— bridge or a —(CH$_2$)$_2$—O—(CH$_2$)$_2$— bridge,
$R^6$ is alkyl and
$X^\ominus$ is Cl$^\ominus$, Br$^\ominus$, I$^\ominus$, CH$_3$SO$_4^\ominus$ or C$_2$H$_5$SO$_4^\ominus$, a process for their preparation from Mannich bases of the formula

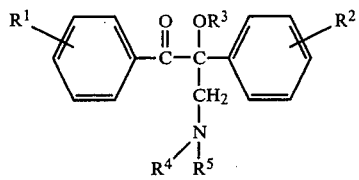

and alkylating agents, and the use of these quaternary ammonium compounds as initiators for the photopolymerization of polymerizable mixtures containing olefinically unsaturated compounds, especially for the preparation of aqueous polymer dispersions or polymer solutions.

7 Claims, No Drawings

BENZOIN PHOTOINITIATOR CONTAINING A QUATERNARY AMMONIUM GROUP IN PHOTO CURABLE COMPOSITION AND PROCESS

The present invention relates to benzoin derivatives containing a quaternary ammonium group, to a process for the preparation of these compounds and to their use as sensitizers for the photopolymerization of polymerizable systems which contain olefinically unsaturated compounds, especially for the preparation of aqueous polymer dispersions and solutions.

Mixtures, polymerizable by UV irradiation, of olefinically unsaturated compounds, conventional additives and photoinitiators have been disclosed and are used in industry, for example to produce coatings or photopolymer printing plates. A plurality of photoinitiators has been proposed in the patent literature and some, eg. α-diketones and their derivatives, acyloins and their derivatives, aromatic disulfides and aromatic carbonyl compounds containing halogen or sulfur, have already been used in practice.

In the case of UV-initiated polymerization in aqueous systems, for example photochemical emulsion polymerization, there is an urgent need for sufficiently water-soluble photoinitiators. The photoinitiators hitherto disclosed for this purpose in the patent literature, for example chlorophyll, xanthophyll or β-carotin combined with ascorbic acid, benzoin, acetoin or α,α'-azodiisobutyramide, suffer from substantial disadvantages. For example, when using these photoinitiators the polymerization conversion is low and/or the polymerization time is very long. If β-carotin, chlorophyll or xanthophyll is used in combination with ascorbic acid, the polymers undergo undesirable discolorations.

U.S. Pat. No. 2,666,025 describes a photopolymerization process whereby polymers having a high molecular weight and a narrow molecular weight distribution are obtained from a small group of vinyl monomers. The monomers claimed carry a substituent, especially alkyl or halogen, on the non-terminal α-carbon atom of the vinyl group. The process consists in irradiating these vinyl monomers with light for several hours, without using an initiator, and then completing the polymerization in the dark for several hours or days. It is true that photosensitizers, eg. lead tetraethyl, diacetyl, phenylglyoxal, glyoxal, acetone and aliphatic azo compounds are mentioned, but no comment is made on the activity of these sensitizers. The process described has the disadvantage of only being applicable to a limited number of monomers. The emulsions are produced as 25% strength batches. Furthermore, the polymerization rate is low, as shown by the Examples, namely 2% conversion/hour. Long polymerization times are needed to give high molecular weights. For example, polymerization for 30 hours at 50° C. is necessary to give a molecular weight of $4 \times 10^6$.

U.S. Pat. No. 3,001,922 concerns the photopolymerization of olefinically unsaturated monomers using α,α'-azodiisobutyramide as the photoinitiator. For example, an aqueous emulsion containing 15% by weight of monomer was photopolymerized. After continuous irradiation for 1 hour, the solids content was only 0.31% by weight. With intermittent irradiation, a solids content of only 2.1% by weight was reached after one hour.

However, for industrial purposes aqueous polymer dispersions having solids contents of from 30 to 60% by weight are required, and these solids contents should be achievable within acceptable polymerization times. The residual monomer content should be very low. Furthermore, the dispersions should be stable on storage.

It is an object of the present invention to provide water-soluble photoinitiators by means of which colorless polymers can be produced by UV irradiation, within an acceptable time and with high conversion.

We have found that this object is achieved by providing the quaternary ammonium compounds according to the invention.

The present invention relates to quaternary ammonium compounds of the formula (I)

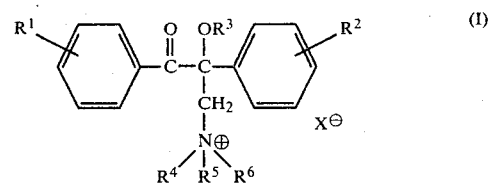

where
$R^1$ and $R^2$ are identical or different and each is H, halogen, phenyl, $C_1$–$C_6$-alkyl, $C_1$–$C_6$-alkoxy or $C_1$–$C_6$-alkylthio,
$R^3$ is H, $C_1$–$C_6$-alkyl, hydroxyalkyl, cycloalkyl or aralkyl,
$R^4$ and $R^5$ are identical or different and each is $C_1$–$C_6$-alkyl, phenyl, cycloalkyl or aralkyl or
$R^4$ and $R^5$ together are a —(CH$_2$)$_4$— bridge, a —(CH$_2$)$_5$— bridge or a —(CH$_2$)$_2$—O—(CH$_2$)$_2$—bridge,
$R^6$ is $C_1$–$C_6$-alkyl and
$X^\ominus$ is $Cl^\ominus$, $Br^\ominus$, $I^\ominus$ or $CH_3SO_4^\ominus$.

The present invention further relates to a process for the preparation of these quaternary ammonium compounds from Mannich bases of the general formula (II)

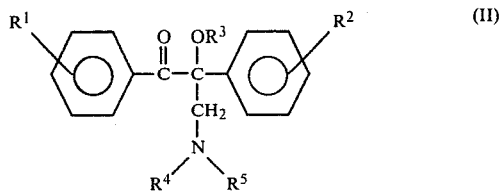

where $R^1$ to $R^5$ have the above meanings, and alkylating agents of the general formula $R^6$–X where $R^6$ is $C_1$–$C_6$-alkyl, and X is Cl, Br, I, SO$_4$CH$_3$ or SO$_4$C$_2$H$_5$, in the presence of an aprotic solvent.

The present invention further relates to the use of the novel quaternary ammonium compounds as initiators for the photopolymerization of photopolymerizable mixtures containing olefinically unsaturated compounds, in particular for the preparation of aqueous polymer dispersions or polymer solutions.

The quaternary ammonium compounds according to the invention are novel. They can be prepared from the Mannich bases. The latter are obtainable from benzoins or benzoinethers by a Mannich reaction with formaldehyde and secondary amines, as described by W. Ried and G. Keil, Ann. 605 (1957), 167 et seq.. Some of the Mannich bases (especially 1,2-diphenyl-2-hydroxy-3-dimethyl-amino-propan-1-one) can also be synthesized by a method similar to that described by G. Kinast and L. F. Tietze, Angew. Chemie 88 (1976), 261.

These Mannich bases can be alkylated, according to the invention, with conventional alkylating agents, eg. methyl bromide or dimethyl sulfate, to give the novel ammonium compounds.

The alkylation is advantageously carried out in an aprotic solvent at from 0° to 100° C., preferably from 20° to 70° C.

In the novel quaternary ammonium compounds, the radicals $R^1$ and $R^2$ can be in the ortho, para or meta position of the phenyl groups of the benzoin structure. Examples of suitable radicals $R^1$ and $R^2$ are hydrogen, chlorine, bromine, phenyl, methyl, ethyl, butyl, tert.-butyl, propyl, iso-propyl, methoxy, ethoxy, methylthio, ethylthio and butylthio; preferred radicals $R^1$ and $R^2$ are H and methyl.

Examples of radicals $R^3$ are hydrogen, methyl, ethyl, hydroxyethyl, hydroxypropyl, cyclohexyl and phenyl, preferably H and $CH_3$.

Examples of radicals $R^4$ and $R^5$ are methyl, ethyl, propyl, cyclohexyl and benzyl; preferred radicals $R^4$ and $R^5$ are methyl and the structures which together with the nitrogen atom form the rings

Examples of suitable radicals $R^6$ are methyl, ethyl, propyl and butyl, the first-mentioned being preferred Examples of the novel quaternary ammonium compounds are:

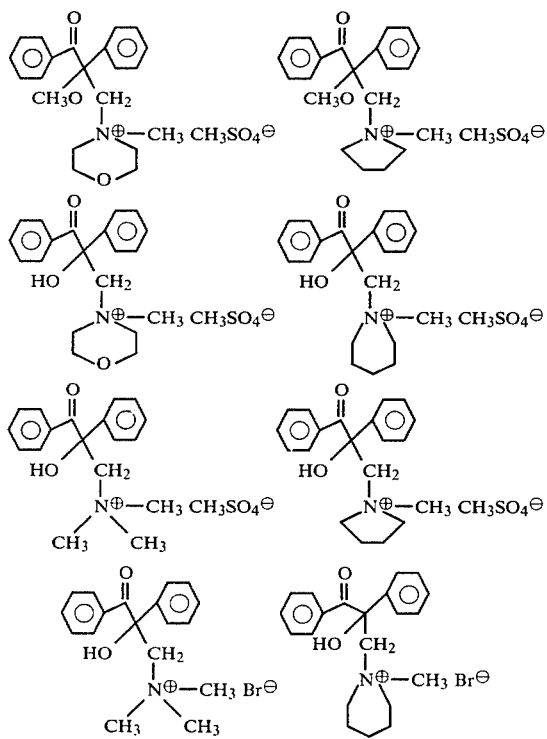

The quaternary ammonium compounds according to the invention may be used as photoinitiators for the photopolymerization of polymerizable mixtures con-taining olefinically unsaturated compounds, especially mixtures which contain water as the solvent or diluent.

They may be used, for example, for the photopolymerization of polyvinyl alcohol-based printing plates, and especially for the photopolymerization of aqueous emulsions or solutions of olefinically unsaturated monomers, in which case industrially useful aqueous polymer dispersions and aqueous solution polymers are obtained with acceptable reaction times and with high conversion.

Stable aqueous polymer dispersions with high solids contents can be prepared by the action of UV light on aqueous emulsions of olefinically unsaturated monomers in the presence of emulsifiers and/or protective colloids and of the quaternary ammonium compounds according to the invention as photoinitiators.

Equally, solution polymers of high molecular weight and having a low residual monomer content can be prepared from aqueous solutions of water-soluble olefinically unsaturated monomers by irradiation with UV light in the presence of the quaternary ammonium compounds according to the invention.

Using the photoinitiators according to the invention, conversions of 98–100% are achieved without additional peroxides or redox initiators. The solution polymers are homogeneous and exhibit no discoloration.

Suitable solvents for use according to the invention are any of the conventional solvents, eg. dimethylformamide, acetone, tetrahydrofuran, hydrocarbons, alcohols, ethyl acetate and the like, but water is preferred.

The use, according to the invention, of the quaternary ammonium compounds to prepare polymer dispersions and polymer solutions has the following additional advantages: The polymerization can be controlled not only by cooling but also by switching the lamp on and off. When it is switched off, the polymerization ceases; when it is switched on again, the polymerization again proceeds. The polymerization temperature can be chosen at will, within a wide range. The polymerization times are in general shorter than with conventional systems and the dispersions or solution polymers prepared by the process according to the invention contain less electrolyte, since electrolytes are always formed as decomposition products of conventional initiator systems.

Suitable olefinically unsaturated photopolymerizable compounds are the conventional monomers, for example monoolefins and diolefins, eg. ethylene, butadiene, isoprene and chloroprene, olefinically unsaturated carboxylic acid esters, eg. esters of acrylic acid and methacrylic acid with alkanols of 1 to 12 carbon atoms, or vinyl esters of fatty acids of 2 to 20 carbon atoms, vinyl halides and vinylidene halides, especially vinyl chloride and vinylidene chloride, vinyl-aromatic compounds, eg. styrene, α-methylstyrene and vinyltoluences, and mixtures of such monomers with one another or with $\alpha,\beta$-olefinically unsaturated monocarboxylic acids and dicarboxylic acids, especially acrylic acid or methacrylic acid, maleic acid, fumaric acid and itaconic acid, as well as with their amides, N-methylolamides, N-alkoxymethylamides and nitriles, especially acrylamide, methacrylamide, maleimide, itaconic acid diamide, N-methylolmethacrylamide, N-methylolacrylamide, N-methoxymethylacrylamide, N-n-butoxymethylacrylamide, N-methoxymethylmethacrylamide, methylene-bis-acrylamide, acrylonitrile and methacrylonitrile. The proportion of such comonomers containing reactive groups, for example carboxyl groups, in the copolymers is in general from 0.2 to 15, preferably from 1 to 10, % by weight, based on the said polymers. Other comonomers which may be used in minor amounts, especially of from 0.2 to 5% by weight, based on the polymers, are glycol monoacrylate and diacrylate, butane-1,4-diol monoacrylate and diacrylate and 3-chloro-2-hydroxypropyl acrylate and methacrylate.

Examples of ethylenically unsaturated carboxylic acid esters of particular interest for use in the polymers are methyl acrylate, ethyl acrylate and methacrylate, isopropyl acrylate, n-butyl acrylate, isobutyl acrylate, tert.-butyl acrylate, 2-ethylhexyl acrylate and methacrylate, vinyl acetate, vinyl propionate, vinyl laurate, vinyl stearate and vinyl esters of branched saturated carboxylic acids, for example of pivalic acid.

Aqueous polymer dispersions of particular interest are those which contain polymers or copolymers which are derived from esters of acrylic acid and/or methacrylic acid with alkanols of 1 to 8 carbon atoms and/or from vinyl esters of saturated monocarboxylic acids of 2 to 12 carbon atoms or from mixtures of butadiene with styrene and/or acrylonitrile and which preferably contain, as copolymerized units, from 0.5 to 5% by weight, based on the polymers, of $\alpha,\beta$-olefinically unsaturated carboxylic acids of 3 to 5 carbon atoms, of the above type.

Aqueous polymer solutions which contain polymers or copolymers of acrylic acid, methacrylic acid, acrylamide, methacrylamide, N-alkanolamides of acrylic acid and/or methacrylic acid and/or water-soluble hydroxyalkyl acrylates are also of particular interest.

The emulsifiers generally employed for the preparation, according to the invention, of aqueous polymer dispersions are ionic and/or nonionic emulsifiers, for example polyglycol ethers, sulfonated paraffin hydrocarbons, higher alkylsulfates, eg. a lauryl-sulfate, alkali metal salts of fatty acids, eg. sodium stearate and sodium oleate, sulfuric acid esters of fatty alcohols, oxyethylated $C_8$-$C_{12}$-alkylphenols, in general containing from 5 to 30 ethylene oxide units, and their sulfonation products, and sulfosuccinic acid esters; the amount of emulsifier used is from 0.1 to 10.0% by weight, based on the monomers. In addition, a protective colloid is used in some cases. Examples of suitable protective colloids are polyvinyl alcohol, partially hydrolyzed polyvinyl acetates, cellulose derivatives, copolymers of methyl acrylate with acrylamide and methacrylamide or vinyl pyrrolidone polymers, in amounts of from about 0.5 to 10, especially from 1.0 to 5, % by weight based on the monomers.

The photoinitiators according to the invention are employed in concentrations of from 0.001 to 10% by weight, preferably from 0.01 to 1% by weight, based on the olefinically unsaturated compounds. In this concentration range, the photoinitiators dissolve completely in water.

One or more of the photoinitiators mentioned can be employed. The photoinitiator can be a component of the initial mixture, but can also be run in as a solution in water.

Radiation sources which can be used to carry out the photopolymerization are lamps which at least partly emit in the region from 2,000 to 5,000 Å, preferably from 3,000 to 4,000 Å. It is advantageous to use mercury vapor lamps, fluorescent lamps, xenon lamps, tungsten lamps, fluorescent tubes or carbon arc lamps.

A photopolymerization using the photoinitiators according to the invention can be carried out batchwise or continuously. The individual components are emulsified or dissolved by conventional methods. These emulsions or solutions are then irradiated with light. The heat of polymerization can be removed by external cooling or by evaporative cooling. The period of irradiation depends on the manner in which it is carried out, on the nature and concentration of the monomers employed, on the nature and amount of the photoinitiators employed, on the intensity of the light source and on the size of the batch and can be from 5 minutes to 4 hours, preferably from 10 minutes to 3 hours.

The polymerization temperature can be selected at will and can be from +5 to about 100° C. Polymerization temperatures of from 10° to 40° C. are particularly preferred.

The solids contents of the dispersions prepared according to the invention are from 5 to 60% by weight, in general from 30 to 50% by weight. The residual monomer content is low. The Fikentscher K-values of the dispersions obtained are high, in general >90. The dispersions prepared by the process according to the invention are exceptionally suitable for coating paper, nonwovens and leather. They can also be used in paints and as adhesives.

The solution polymers prepared by the process according to the invention are distinguished by high molecular weights, ie. Fikentscher K-values of about 90. They are exceptionally suitable for use as flocculating agents for effluent purification, as assistants in the manufacture of paper and in the textile industry, and as assistants for tertiary oil production.

In the Examples, parts and percentages are by weight, unless stated otherwise.

I. PREPARATION OF THE MANNICH BASES

A: 84 parts of benzoin, 42 parts of 40% strength formaldehyde solution and 31.2 parts of pyrrolidine are refluxed for 10 hours and stirred overnight. After boiling up again, in the presence of ethanol, the solution is left to crystallize. The precipitate is filtered off. Recrystallization from ethanol gives 57.2 parts (49%) of crystalline 1,2-diphenyl-2-hydroxy-3-(N-pyrrolidino)-propan-1-one (the structure being confirmed by NMR and analysis).

B: 84 parts of benzoin, 37.5 parts of piperidine and 42 parts of 40% strength formaldehyde solution are refluxed for 2 hours and the mixture is left to crystallize out. After twice recrystallizing from ethanol, 91 parts (74%) of 1,2-diphenyl-2-hydroxy-3-(N-piperidino)-propan-1-one, melting point 69°–70° C., are obtained (the structure being confirmed by NMR and analysis).

C: 84 parts of benzoin, 40 parts of morpholine and 42 parts of 40% strength formaldehyde solution are refluxed for 5½ hours and then left to stand overnight at room temperature. After recrystallization from ethanol, 88 parts (71.5%) of 1,2-diphenyl-2-hydroxy-3-(N-morpholino)-propan-1-one, melting point 95°–97° C., are obtained (the structure being confirmed by NMR and analysis).

D: 22.6 parts of benzoin methyl ether, 10.5 parts of 40% strength formaldehyde solution and 9.4 parts of piperidine are refluxed for 6 hours, the mixture is taken up in chloroform, the solution is concentrated and the residue is twice recrystallized from methanol. Yield, 10.1 parts (33%) of crystalline 1,2-diphenyl-2-methoxy-3-(N-piperidino)-propan-1-one, melting point 88° C. (the structure being confirmed by NMR and analysis).

E: 22.6 parts of benzoin methyl ether, 10.5 parts of 40% strength formaldehyde solution and 10 parts of morpholine are refluxed for 6 hours. When the mixture has cooled, the crystals which have precipitated are repeatedly recrystallized from ethanol. Yield, 12.6 parts (39%) of 1,2-diphenyl-2-methoxy-3-(N-morpholino)-propan-1-one, melting point 95° C. (the structure being confirmed by NMR and analysis).

II. PREPARATION OF THE QUATERNARY AMMONIUM COMPOUNDS

Example 1

30 parts of 1,2-diphenyl-2-hydroxy-3-(N-pyrrolidino)-propan-1-one, dissolved in 80 parts of nitromethane, are mixed with 14.5 parts of dimethyl sulfate, dissolved in 30 parts of nitromethane, and the mixture is kept at 60° C. for 2 hours. The precipitate is filtered off and recrystallized from ethanol. Yield, 18.9 parts (45%) of 1,2-diphenyl-2-hydroxy-3-[N-(N-methyl)-pyrrolidinium]-propan-1-one methyl-sulfate, melting point 184° C. (the structure being confirmed by NMR and analysis).

Example 2

5.1 parts of 1,2-diphenyl-2-hydroxy-3-(N-piperidino)-propan-1-one are mixed with 2.1 parts of dimethyl sulfate in 20 parts of dioxane. The solution is stirred for 5 days at room temperature. The crystals which have precipitated are filtered off and washed with dioxane; yield, 2.3 parts (32%) of water-soluble, crystalline 1,2-diphenyl-2-hydroxy-3-[N-(N-methyl)-piperidinium]-propan-1-one methyl-sulfate, melting point 160°–161° C. (the structure being confirmed by NMR and analysis).

Example 3

30 parts of 1,2-diphenyl-2-hydroxy-3-(N-morpholino)-propan-1-one, dissolved in 80 parts of nitromethane, are mixed with 14.5 parts of dimethyl sulfate, dissolved in 30 parts of nitromethane, and the mixture is refluxed for 4½ hours. After having been filtered off, the precipitate is recrystallized from water; yield, 18.9 parts (45%) of white crystals of 1,2-diphenyl-2-hydroxy-3-[N-(N-methyl)-morpholinium]-propan-1-one methyl-sulfate, melting point 204° C. (the structure being confirmed by NMR and analysis).

Example 4

6.5 parts of 1,2-diphenyl-2-methoxy-3-(N-morpholino)-propan-1-one are mixed with 2.6 parts of dimethyl sulfate in 30 parts of dioxane and the mixture is stirred for 2 hours at 60° C. To complete the reaction, a further 0.7 part of dimethyl sulfate is added and stirring is continued for 45 minutes. After concentrating the reaction mixture, the crystals which have precipitated are filtered off and recrystallized from cyclohexane/ethanol. Yield, 5 parts (55%) of 1,2-diphenyl-2-methoxy-3[N-(N-methyl)-morpholinium]-propan-1-one methyl-sulfate, melting point 174° C. (the structure being confirmed by NMR and analysis).

III. EMULSION POLYMERIZATION

Example 5

A monomer emulsion is prepared, in a conventional mixing apparatus, from 50 parts of methyl acrylate, 50 parts of ethyl acrylate, 1.3 parts of 40% strength $C_{15}$-paraffinsulfonate, 1.3 parts of a 20% strength adduct of isooctylphenol and 25 ethylene oxide units and 210 parts of water.

The UV light source (Philips HPK 125 watt) is contained in a lamp sleeve, made of Duran glass, in a glass vessel equipped with a thermometer and stirrer. To remove the heat of polymerization, the reaction vessel is cooled with cooling fluid by means of an outer cooling jacket. The lamp sleeve is cooled with water. After introducing the monomer emulsion into the reaction vessel, the latter is flushed with nitrogen. Initially, the reaction mixture is at 15° C. After adding 0.17 part of photoinitiator

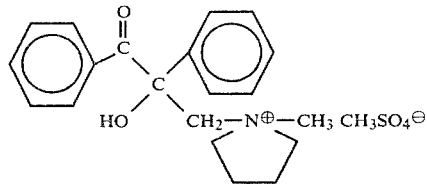

(=0.17% based on monomers) in 6.7 parts of water, the mixture is irradiated. The start of the polymerization manifests itself in a temperture rise. The reaction temperature is kept at from 15° to 30° C. by means of the cooling system. The irradiation time is 60 minutes and the resulting aqueous polymer dispersion has a solids content of 30%.

Residual monomer content: 0.07% of methyl acrylate, 0.02% of ethyl acrylate. K value of the copolymer: 153.6.

Example 6

A monomer emulsion of 50 parts of methyl acrylate, 50 parts of butylacrylate, 2 parts of 40% strength $C_{15}$-paraffinsulfonate, 2 parts of a 20% strength adduct of isooctylphenol and 25 ethylene oxide units and 89 parts of water is mixed with 0.1 part of the photoinitiator mentioned in Example 5 (=0.1% based on monomers), dissolved in 4 parts of $H_2O$, and photopolymerization is carried out as described in Example 5. After an irradiation time of 3 hours, an aqueous polymer dispersion having a solids content of 48.5% is obtained.

Residual monomer content: 0.1% of butyl acrylate, 0.07% of methyl acrylate. K value of the copolymer: 142.2.

Example 7

A monomer emulsion of 95 parts of n-butyl acrylate, 5 parts of acrylic acid, 1 part of a 15% strength alkylarylsulfonate, 0.33 part of a 20% strength adduct of isooctylphenol and 25 ethylene oxide units and 90 parts of water is emulsified in the apparatus mentioned in Example 5 and after adding 0.1 part of the photoinitiator mentioned in Example 5, dissolved in 4 parts of water (=0.1% of photoinitiator, based on monomers), the mixture is irradiated. The reaction temperature is 15°–20° C. The total period of irradiation is 180 minutes. An aqueous polymer dispersion having a solids content of 49% is obtained.

Residual monomer content: 0.1% of butyl acrylate. K value of the copolymer: 165.

Example 8

A monomer emulsion is prepared from 50 parts of n-butyl acrylate, 49 parts of ethyl acrylate, 1 part of 45% strength N-methylolmethacrylamide, 1.3 parts of 40% strength $C_{15}$-paraffinsulfonate and 107 parts of water in the apparatus described in Example 5, and nitrogen is passed through the emulsion. A solution of 0.05 part of the photoinitiator mentioned in Example 5 (0.05% based on monomers), dissolved in 2 parts of water, is then added and the mixture is irradiated with UV light. The polymerization time is 135 minutes. The polymer dispersion has a solids content of 46%.

Residual monomer content: 0.1% of butyl acrylate, 0.12% of ethyl acrylate.

Example 9 and Comparative Examples

A monomer emulsion is prepared from 75 parts of butyl acrylate, 17 parts of methyl methacrylate, 4 parts of acrylic acid, 4 parts of a sulfonated adduct of isooctylphenol and 25 ethylene oxide units, in the form of a 35% strength solution in $H_2O$, and 149 parts of water.

0.23 part (0.24%, based on monomers) of one of various initiators is dispersed in the monomer emulsion and the latter is irradiated as described in Example 5. The progress of the reaction is followed by determining the solids content. After completion of the reaction, the mixture is poured through a coarse mesh filter to remove the coagulate formed. The properties of the polymer dispersions thus obtained are shown in the Table.

In contrast to the initiator I according to the invention, the other initiators, which are prior art initiators, do not give stable dispersions and also do not give such high K values.

| Initiator | Duration of reaction (exposure time) | Solids content theoretical | Solids content found | Amount of coagulate Immediately | Amount of coagulate After 3 months | K value |
|---|---|---|---|---|---|---|
| Benzil dimethylketal | 3.5 hours | 39% | 38% | 12 g | Dispersion sediments[xx] | 92 |
| Benzoin isopropyl ether | 7 hours[x] | 39% | 36% | 18 g | Dispersion sediments[xx] | 112 |
| β-(Benzoin ethyl ether)-propionic acid | 3 hours | 39% | 36.5% | 10 g | Dispersion sediments[xx] | 130 |
| Initiator I (according to the invention) | 3 hours | 39% | 39% | 1 g | — | 140 |

Initiator I = 1,2-diphenyl-2-hydroxy-3-[N-(N-methyl)-pyrrolidinium]-propan-1-one methyl-sulfate
[x] A heavy deposit forms on the lamp sleeve.
[xx] A coagulated sediment forms.

IV. SOLUTION POLYMERIZATION

Example 10

A solution of 70 parts of acrylic acid, 130 parts of acrylamide, 1,800 parts of water and 1 part of the photoinitiator mentioned in Example 5 (0.5% based on monomers) is polymerized with UV light, at 25°–30° C., in the apparatus described in more detail in Example 5. After an irradiation time of 60 minutes, a very viscous, colorless polymer solution results.

Solids content: 10%.
K value: 92.

We claim:

1. A photopolymerizable mixture which comprises: at least one olefinically unsaturated compound and at least one photoinitiator of the formula I

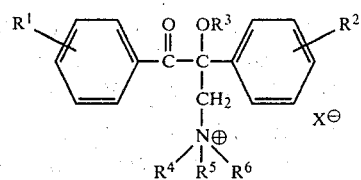

where
$R^1$ and $R^2$ are identical or different and each is H, halogen, phenyl, $C_1$-$C_6$-alkyl, $C_1$-$C_6$-alkoxy or $C_1$-$C_6$-alkylthio,
$R^3$ is H, $C_1$-$C_6$-alkyl, hydroxyalkyl, cycloalkyl or aralkyl,
$R^4$ and $R^5$ are identical or different and each is $C_1$-$C_6$-alkyl, phenyl, cycloalkyl or aralkyl or
$R^4$ and $R^5$ together are a —$(CH_2)_4$—bridge, a —$(CH_2)_5$—bridge or a —$(CH_2)_2$—O—$(CH_2)_2$—bridge,
$R^6$ is $C_1$-$C_6$-alkyl and
$X^\ominus$ is $Cl^\ominus$, $Br^\ominus$, $I^\ominus$ or $CH_3SO_4^\ominus$.

2. In a process for photopolymerizing a photopolymerizable mixture containing at least one olefinically unsaturated compound and at least one photoinitiator, wherein said mixture is irradiated to initiate the polymerization, the improvement which comprises: using as the photoinitiator at least one quaternary ammonium compound of the formula I

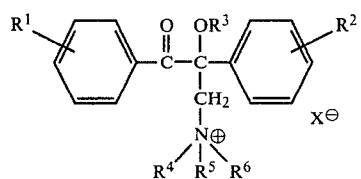

where
$R^1$ and $R^2$ are identical or different and each is H, halogen, phenyl, $C_1$-$C_6$-alkyl, $C_1$-$C_6$-alkoxy or $C_1$-$C_6$-alkylthio,
$R^3$ is H, $C_1$-$C_6$-alkyl, hydroxyalkyl, cycloalkyl or aralkyl,
$R^4$ and $R^5$ are identical or different and each is $C_1$-$C_6$-alkyl, phenyl, cycloalkyl or aralkyl or
$R^4$ and $R^5$ together are a —$(CH_2)_4$—bridge, a —$(CH_2)_5$—bridge or a —$(CH_2)_2$—O—$(CH_2)_2$—bridge,
$R^6$ is $C_1$-$C_6$-alkyl and $X^\ominus$ is $Cl^\ominus$, $Br^\ominus$, $I^\ominus$ or $CH_3SO_4^\ominus$.

3. The process of claim 2 wherein from 0.001 to 10, preferably from 0.01 to 1, percent by weight, based on the olefinically unsaturated compounds, of the quaternary ammonium compound is employed.

4. The process of claim 2 wherein the radiation source used for the photopolymerization emits at least partially in the region from 2,000 to 5,000 Å, preferably from 3,000 to 4,000 Å.

5. The process of claim 2, wherein an aqueous photopolymerizable mixture is photopolymerized to form an aqueous polymer dispersion or polymer solution.

6. The process of claim 5, wherein from 0.001 to 10, preferably from 0.01 to 1, percent by weight, based on the olefinically unsaturated compounds, of the quaternary ammonium compound is employed.

7. the process of claim 5 wherein the radiation source used for the photopolymerization emits at least partially in the region from 2,000 to 5,000 A, preferably from 3,000 to 4,000 Å.

* * * * *